(12) United States Patent
Latham et al.

(10) Patent No.: US 9,205,379 B2
(45) Date of Patent: *Dec. 8, 2015

(54) INSTRUMENT FOR INDEPENDENT ELECTROTRANSFER IN MULTIPLE CASSETTES

(71) Applicant: Bio-Rad Laboratories, Inc., Hercules, CA (US)

(72) Inventors: Matthew Latham, Dixon, CA (US); William Strong, El Cerrito, CA (US); Nikolas Chmiel, Fairfield, CA (US); Jeff Xu, Alameda, CA (US); Robert Iovanni, Vallejo, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/229,564

(22) Filed: Mar. 28, 2014

(65) Prior Publication Data
US 2014/0339084 A1    Nov. 20, 2014

Related U.S. Application Data

(63) Continuation of application No. 12/963,430, filed on Dec. 8, 2010, now Pat. No. 8,715,476.

(60) Provisional application No. 61/285,661, filed on Dec. 11, 2009.

(51) Int. Cl.
*B29C 35/02* (2006.01)
*B01D 57/02* (2006.01)
*G01N 27/447* (2006.01)

(52) U.S. Cl.
CPC .......... *B01D 57/02* (2013.01); *G01N 27/44739* (2013.01)

(58) Field of Classification Search
CPC .................. B01D 57/02; G01N 27/44739
USPC .................. 204/450–470, 600–621
See application file for complete search history.

(56) References Cited

U.S. PATENT DOCUMENTS

| 4,840,714 A | 6/1989 | Littlehales |
| 5,104,512 A | 4/1992 | Gombocz et al. |

(Continued)

FOREIGN PATENT DOCUMENTS

| JP | 55-106859 U | 7/1980 |
| JP | 04-137800 A | 5/1999 |

(Continued)

OTHER PUBLICATIONS

International Search Report and Written Opinion from PCT/US2010/059756, dated Feb. 15, 2011.

(Continued)

*Primary Examiner* — Bach Dinh
(74) *Attorney, Agent, or Firm* — Kilpatrick Townsend & Stockton LLP

(57) ABSTRACT

Electrotransfer is performed in an instrument that receives electroblotting cassettes and that contains an integrated power supply, controls, and a display that allows the user to monitor and control each of a plurality of cassettes individually through electrical contacts within the housing that mate with corresponding electrical contacts on the cassettes.

9 Claims, 4 Drawing Sheets

(56) References Cited

U.S. PATENT DOCUMENTS

| | | | |
|---|---|---|---|
| 5,149,408 | A | 9/1992 | Perlman et al. |
| 5,445,723 | A | 8/1995 | Camacho |
| 5,892,020 | A | 4/1999 | Mezes et al. |
| 5,988,371 | A | 11/1999 | Paley et al. |
| 6,001,187 | A | 12/1999 | Paley et al. |
| 6,007,689 | A | 12/1999 | Renfrew et al. |
| 6,062,381 | A | 5/2000 | Paley et al. |
| 6,207,227 | B1 | 3/2001 | Russo et al. |
| 6,308,538 | B1 | 10/2001 | Wood et al. |
| 6,770,581 | B1 | 8/2004 | DeMott et al. |
| 6,969,615 | B2 | 11/2005 | Knezevic et al. |
| 2002/0171910 | A1 | 11/2002 | Pullen et al. |
| 2003/0178312 | A1 | 9/2003 | Amirkhanian et al. |
| 2004/0050699 | A1* | 3/2004 | Goncalves ............... 204/450 |
| 2007/0007140 | A1 | 1/2007 | Zimmerman et al. |
| 2007/0284250 | A1* | 12/2007 | Magnant et al. ........... 204/459 |
| 2009/0026079 | A1 | 1/2009 | Margalit et al. |
| 2010/0120129 | A1* | 5/2010 | Amshey et al. ............ 435/270 |
| 2010/0126863 | A1 | 5/2010 | Stewart, Jr. et al. |
| 2011/0042213 | A1 | 2/2011 | Updyke et al. |

FOREIGN PATENT DOCUMENTS

| | | |
|---|---|---|
| JP | 2004-532384 A | 10/2004 |
| JP | 2004-535557 A | 11/2004 |
| WO | 02/059589 A2 | 8/2002 |
| WO | 02/077630 A1 | 10/2002 |
| WO | 03/078452 A1 | 9/2003 |
| WO | 2005/098408 A1 | 10/2005 |
| WO | 2006/091525 A2 | 8/2006 |
| WO | 2007/106832 A2 | 9/2007 |

OTHER PUBLICATIONS

Office Action from JP Appl. No. 2012-543269, dated Aug. 27, 2013 (Engl. Version).

U.S. Appl. No. 11/955,955, filed Dec. 13, 2007 (17 pages).

Dalton, R.G. et al.; "A new rapid semi-dry blotting technique for multimeric sizing of von willebrand factor"; 1988, *Thrombosis Research*, vol. 50, No. 2, pp. 345-349.

Kurien, B.T. et al.; "Protein blotting: a review"; 2003, *Journal of Immunological Methods*, vol. 274, No. 1-2, pp. 1-15.

Kurien, B.T. et al.; Western blotting; 2006, *Methods*, vol. 38, pp. 283-293.

Supplementary European Search Report from Appl. 10836707.9, dated Jul. 31, 2014.

\* cited by examiner

INSTRUMENT FOR INDEPENDENT ELECTROTRANSFER IN MULTIPLE CASSETTES

CROSS-REFERENCE TO RELATED APPLICATION

This application is a continuation of U.S. patent application Ser. No. 12/963,430, filed on Dec. 8, 2010, which claims the benefit of U.S. Provisional Patent Application No. 61/285,661, filed Dec. 11, 2009, the contents of each of which are incorporated herein by reference.

FIELD OF THE INVENTION

This invention resides in the field of gel electrophoresis, and relates in particular to the transfer of electrophoretically separated species from a slab gel or any other two-dimensional medium in which the species were separated to a two-dimensional support matrix in which the species can be detected, identified, and quantified.

DESCRIPTION OF THE PRIOR ART

Proteins, nucleic acids, or other biological species that have been electrophoretically separated in a slab gel are often transferred to a membrane of nitrocellulose, nylon, polyvinyl difluoride, or similar materials for identification and quantification which are more easily performed on the membrane than in the gel. A common transfer technique is electroblotting, in which the flat surfaces of the gel and membrane are placed in direct contact and an electric current is passed through both the gel and the membrane in a transverse direction, thereby transferring the species in a manner similar to that by which the species were mobilized within the gel. When the species are DNA fragments, the transfer is termed a Southern blot after its originator, the British biologist Edwin M. Southern. By analogy, the transfer of RNA fragments is termed Northern blotting, and the transfer of proteins or polypeptides is termed Western blotting. Once transfer has occurred, the species on the membrane are analyzed by methods appropriate to the species themselves. In Southern and Northern blots, for example, the analysis involves treatment of the species on the membrane with a hybridization probe, followed by labeling them with a fluorescent or chromogenic dye. In Western blots, the species are treated with antibodies, followed by the use of conventional labeling techniques to detect the antibodies.

Electroblotting of the Southern, Northern, and Western types can all be performed in either a wet, dry, or semi-dry format. In wet blotting, the gel and membrane are layered over each other in a stack which is immersed in a transfer buffer solution in a tank on whose walls are mounted wire or plate electrodes. The electrodes are then energized to cause the solutes to migrate from the gel to the membrane. In semi-dry blotting, filter papers wetted with the transfer buffer solution are used, and the stack contains the filter papers on the top and bottom with the gel and the membrane between the filter papers to form a "blotting sandwich." The electrodes are then placed in direct contact with the exposed surfaces of the wetted filter papers. Dry electroblotting uses no liquid buffers other than those residing in the gels. Descriptions of wet, dry, and semi-dry electroblotting and the associated materials and equipment are found in Margalit et al. (Invitrogen) United States Patent Application Publication Nos. US 2006/0272946 A1, published Dec. 7, 2006, US 2006/0278531 A1, published Dec. 14, 2006, and US 2009/0026079 A1, published Jan. 29, 2009; Littlehales (American Bionetics) U.S. Pat. No. 4,840,714, issued Jun. 20, 1989; Dyson et al. (Amersham International) U.S. Pat. No. 4,889,606, issued Dec. 26, 1989; Schuette (Life Technologies, Inc.), U.S. Pat. No. 5,013,420, issued May 7, 1991; Chan et al. (Abbott Laboratories), U.S. Pat. No. 5,356,772, issued Oct. 18, 1994; Camacho (Hoefer Scientific Instruments), U.S. Pat. No. 5,445,723, issued Aug. 29, 2005; Boquet (Bertin & Cie), U.S. Pat. No. 5,482,613, issued Jan. 9, 1996; and Chen (Wealtec Enterprise Co., Ltd.) U.S. Pat. No. 6,592,734, issued Jul. 15, 2003.

SUMMARY OF THE INVENTION

The present invention resides in an instrument that can perform electrotransfer in either a single electrotransfer cassette or in two or more such cassettes simultaneously and independently. The term "electrotransfer cassette" is used herein to mean any receptacle that contains electrodes and can accommodate a gel or other medium that has chemical or biological species distributed therein in a two-dimensional array such as the wells of a microtiter plate, plus a membrane or other two-dimensional matrix to which the species are to be transferred by the influence of the electric field generated by the electrodes. The instrument is particularly suited to cassettes that are designed to perform electroblotting from slab gels. The invention is also well suited to cassettes that have electrical contacts on their exterior surfaces that are electrically connected to the electrodes inside the cassettes. The instrument contains a power supply and uses battery contact technology to connect the power supply with each cassette, thereby allowing the instrument to be used either with its full capacity of cassettes or with only one cassette or a number of cassettes less than the full capacity of the instrument, utilizing only the power needed for the cassette(s) present in the instrument. The battery-style electrical contacts are mounted in the interior of the instrument and inaccessible to the user even when the instrument is empty or has an unoccupied space, thereby avoiding inadvertent exposure of the user to an electric current. Connection of a cassette to the instrument contacts is achieved by simple insertion of the cassette in the instrument, and in certain embodiments of the invention the instrument contains automatic relays that block the power supply to the electrical contacts for each individual cassette when the cassette is removed. In preferred designs, the instrument holds multiple cassettes in a vertical stack, thereby providing the instrument with a small footprint that consumes a minimum of bench space. Further features of the instrument will be apparent from the descriptions that follow and the accompanying figures.

DETAILED DESCRIPTION OF THE INVENTION AND PREFERRED EMBODIMENTS

With electroblotting cassettes as illustrative examples, electroblotting cassettes that can be used with the instrument of the present invention are described in commonly owned U.S. Provisional Patent Application No. 61/285,277, filed Dec. 10, 2009, entitled "Electroblotting Cassette With Integrated Electrical Contacts and Rotary Locking Mechanism" (M. Latham, inventor), and United States Pre-Grant Patent Publication No. US 2010-0213064 A1, published Aug. 26, 2010, entitled "Electroblotting Cassette With Manually Releasable Electrodes of Adjustable Spacing" (M. Latham, inventor). In general, the instrument will receive any electrotransfer cassette that contains external electrical contacts.

Figure 1:
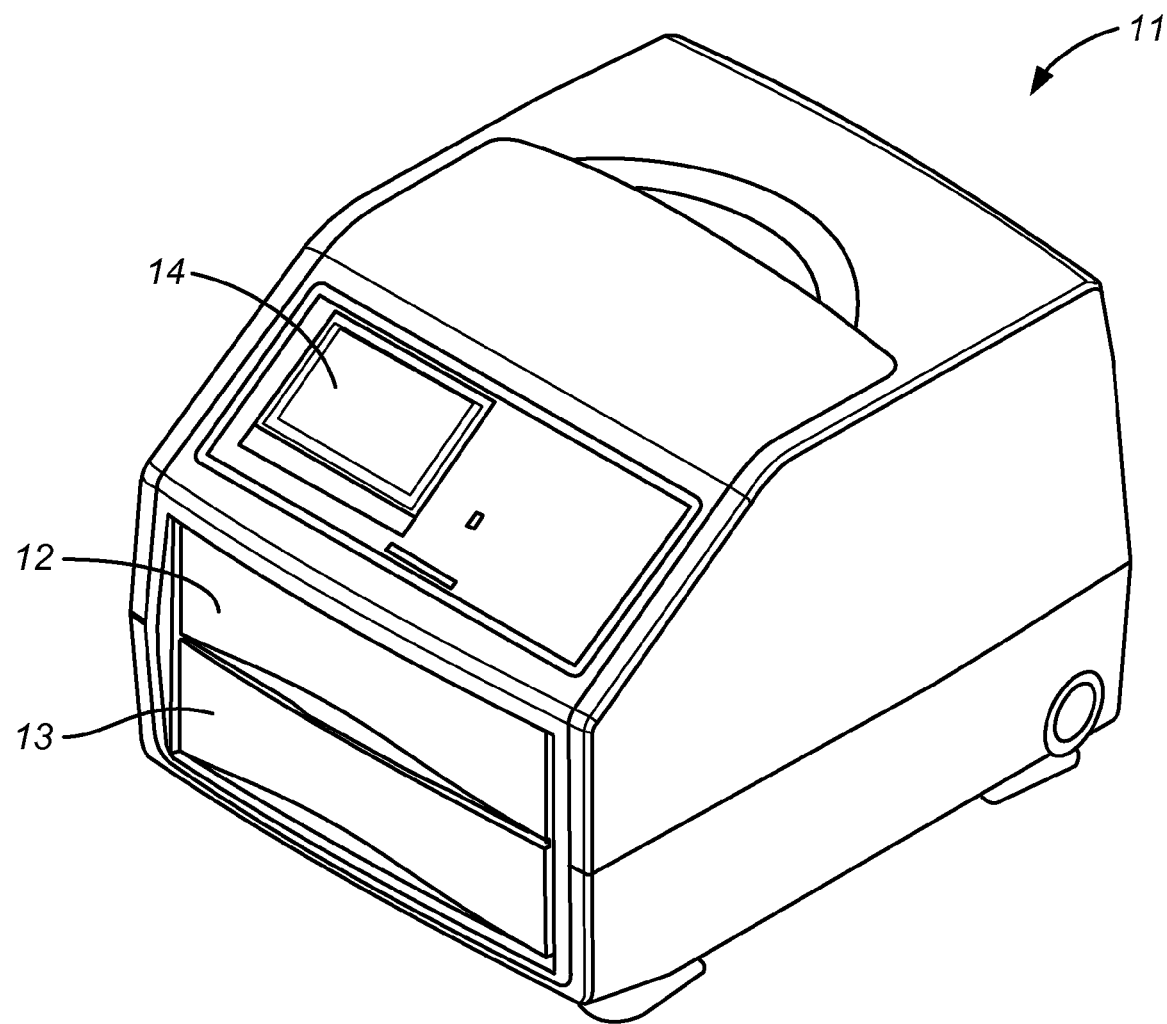
FIG. 1 is a perspective view of an instrument in accordance with the present invention that accommodates two cassettes.
Figure 2:
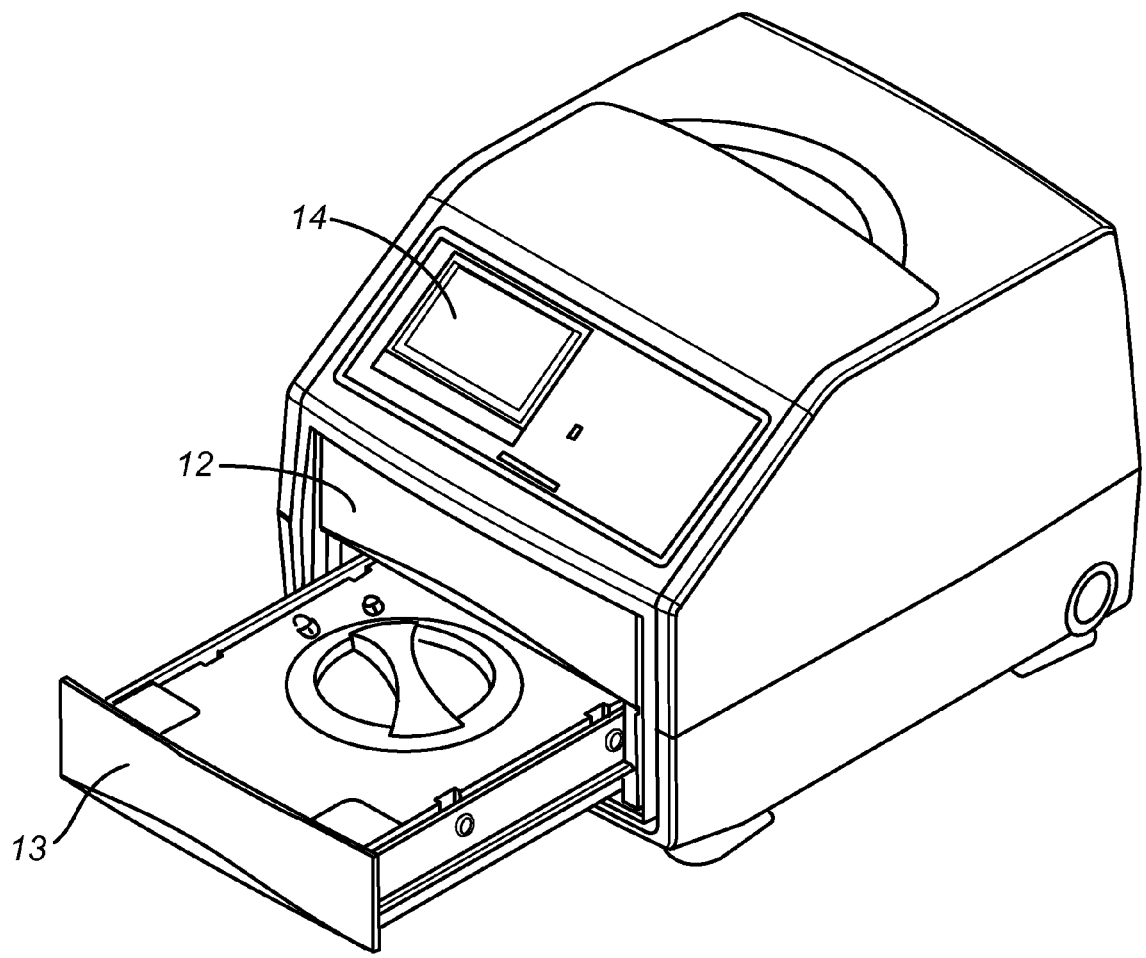
FIG. 2 is a perspective view of the instrument of FIG. 1 with one of the two cassettes fully inserted and another partially inserted.

The instrument 11 shown in FIGS. 1 and 2 holds two such cassettes 12, 13 in a vertical stack. Both are inserted independently by a sliding insertion through slot-shaped openings in the front of the instrument, or through a single opening with guide rails at different heights along the internal walls of the instrument. The lower cassette in FIG. 2 is shown partially inserted for purposes of demonstration. Instruments within the scope of the invention can be constructed to accommodate any number of cassettes, and instruments that accommodate two, three, four, five, or six cassettes will most likely be the most common. The receiving slots or positions can be arranged vertically as shown or horizontally, or in two-dimensional arrays forming columns and rows. The instrument can be operated with cassettes occupying all slots or positions or with one or more slots or positions left unoccupied and therefore unused. The electronics are designed to allow independent control over individual positions and the cassettes occupying those positions.

The front of the instrument contains a display 14 showing the conditions of the electroblotting procedure for each cassette, including timing, voltage, current, and running parameters in general, and optionally additional parameters such as indicators to show the number of inserted cassettes detected by the instrument and failure diagnostics. The display can be a touch screen with incorporated programming controls for individual cassettes. Alternatively, the programming controls can be incorporated in a membrane keypad overlying the display and the adjacent surface of the instrument housing, or a keypad incorporated into the housing itself.

Figure 3:
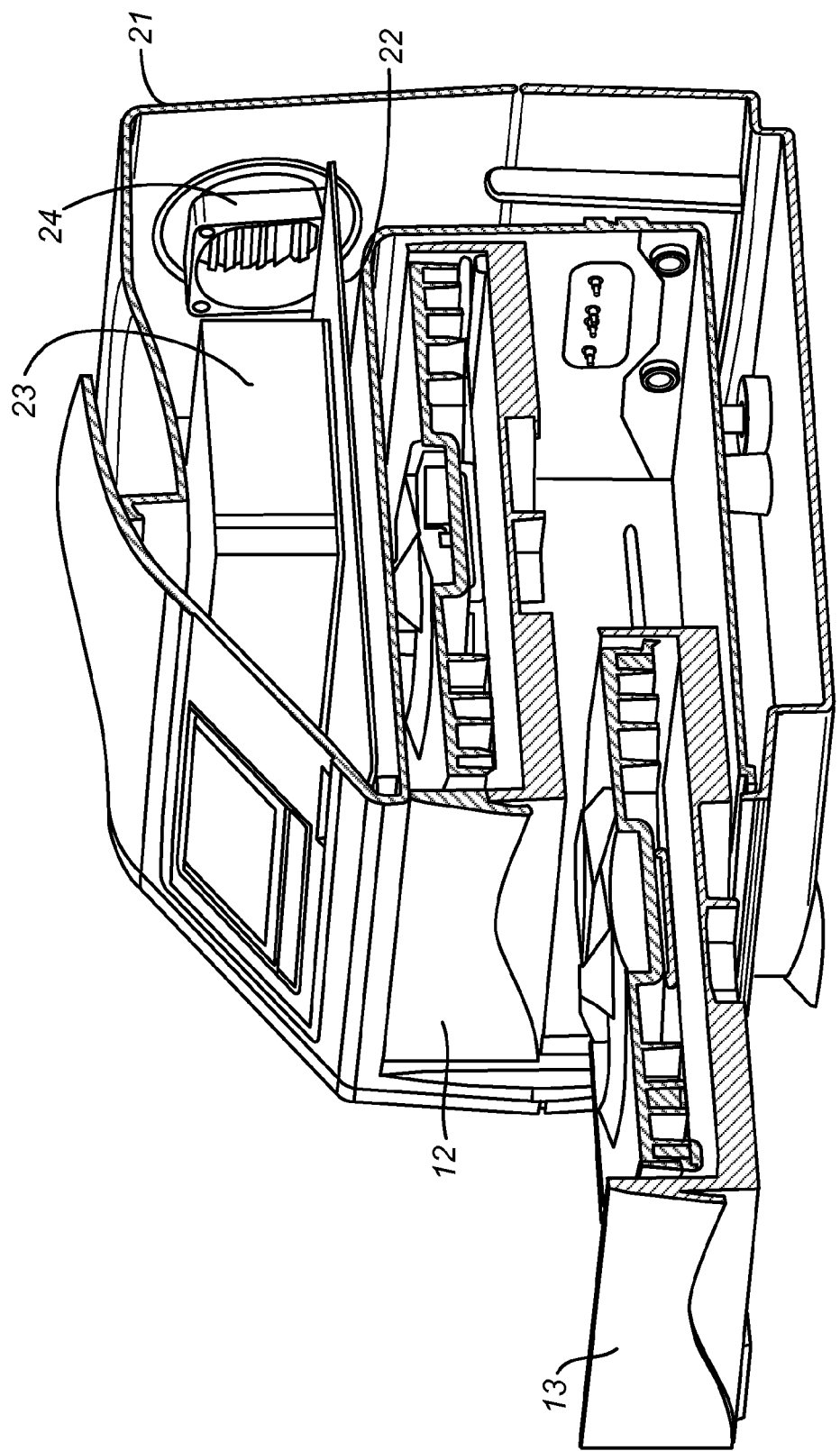
FIG. 3 is a cutaway view of the instrument of FIG. 1.

FIG. 3 shows the instrument housing 21 in a cutaway view, with the upper cassette 12 fully inserted and the lower cassette 13 partially inserted as in FIG. 2. Mounted inside the housing 21 are a printed circuit board 22 and a power supply 23. The power supply 23 can be a common commercially available component such as one with universal input and a 30V dc output. The dc output is directed to amplifiers on the board 22 that control the voltage to each cassette. The amplifiers and other components on the board preferably form a multitude of independent electrical channels, one for each cassette slot. A fan 24 mounted in the rear wall of the housing (only the mounting frame for the fan is shown) cools the electronic components. The power supply 23 and the board 22 in this embodiment are positioned above the upper cassette slot in a stacked arrangement that preserves the small footprint of the instrument and thereby conversed bench space.

Figure 4:
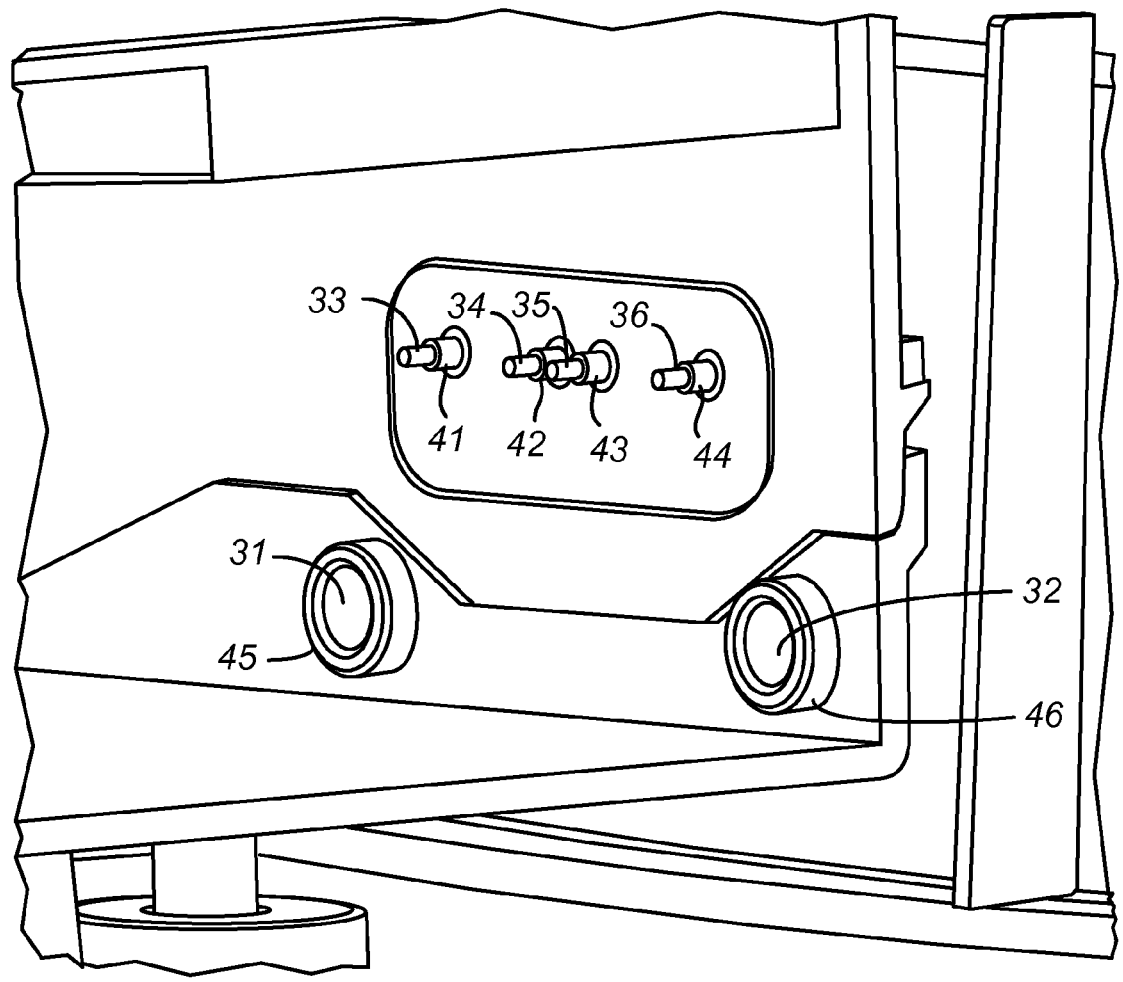
FIG. 4 is an enlarged view of one set of electrical interconnects in the interior of the instrument of FIG. 1.

FIG. 4 is an enlarged view of a portion of the internal surface of the rear wall of the instrument housing. Mounted to this wall are a pair of slugs 31, 32 of magnetically responsive material such as steel. The slugs are aligned with magnets on the rear of each cassette when the cassette is inserted in the instrument, and the slugs and magnets serve to secure the inserted cassette in place. Reed relays are also incorporated into the housing in the region of these slugs to control the activation of the electronics for individual cassette slots upon insertion or removal of a cassette, thereby blocking the power supply to the electrical contacts at each position that is not occupied by a cassette. Any relay that can be activated by insertion of the cassette and deactivated upon removal of the cassette can be used.

Also visible in FIG. 4 are the electrical contacts 33, 34, 35, 36 that supply voltage to the cassette when the cassette is inserted by contacting the electrical contacts on the back of each cassette. Of the many types of contacts that can be used, an example are battery-style contacts, i.e., spring-loaded contacts known in the art as "pogo pins." Voltage is supplied to the contacts by the amplifiers on the board 22. In the embodiment shown, two electrical contacts are included for each electrode in the cassette: the two central pins 34, 35 will engage the single anode contact on the cassette while the two outer pins 33, 36 will engage the two cathode contacts on the cassette that flank the anode contact. A single contact for each electrode will also suffice, although the redundancy of multiple contacts is preferred for a more reliable connection. The number and positions of these pins will be varied to correspond to any variations in the number and spatial arrangement of the contacts on the cassette. The pins are mounted inside rigid sleeves 41, 42, 43, 44, which serve as stops for the cassette and prevent contact between the back end surface of the cassette and the rear wall of the housing. Raised bosses 45, 46 surrounding the steel slugs serve a similar function. The housing can also contain horizontal grooves in the internal surfaces of the side walls of the cassette slots to mate with ridges on the side edges of the cassettes, or vice versa, to help guide the cassettes into the slots. The grooves can eliminate the need for individual slots for the cassettes, and instead allow the housing to be constructed with a single large opening to accommodate the full number of cassettes in a stacked arrangement, with grooves arranged at multiple heights within the opening to position the individual cassettes and to align them with the electronic interconnects at the inner rear wall of the housing.

To utilize an instrument in accordance with the above descriptions in electroblotting procedures for transferring electrophoretically separated species from a slab gel to a sheet-form matrix such as a membrane of nitrocellulose, nylon, polyvinyl difluoride, or other material on which treatments or analysis are typically performed in a biochemical laboratory, the gel and membrane, typically in combination with buffer-wetted filter papers, are first arranged in a stack and placed in a cassette which includes plate electrodes as the anode and cathode plus external electrical contacts. The cassette, together with further cassettes in many cases, is then placed in the instrument, and the instrument is programmed to impose electrical charges on the electrodes to produce an electric field transverse to the planes of the gel and membrane sufficient to cause the species to migrate to the membrane. As explained above, a single cassette can be processed in this manner, or two or more cassettes simultaneously in the same instrument, either under identical or individually controlled conditions.

Further alternatives to the structures, shapes, and arrangements shown in the figures that are still within the concept of the present invention include electrical contacts other than the Pogo pins shown in the Figures, but still either spring-loaded like the Pogo pins, or other resilient or non-resilient configurations that will ensure proper electrical contact. Similarly, electrical actuators other than Reed relays that will shut off power when a cassette is removed can be used, and other variations can be made that will be readily apparent to those skilled in the art.

In the claims appended hereto, the term "a" or "an" is intended to mean "one or more." The term "comprise" and variations thereof such as "comprises" and "comprising,"

when preceding the recitation of a step or an element, are intended to mean that the addition of further steps or elements is not excluded from the scope of the claim. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. An electrotransfer instrument comprising:
   a housing with an internal cavity sized to contain a horizontally oriented electroblotting cassette, said cavity mating with ridges on the side of said cassette;
   a power supply and printed circuit board mounted to and within said housing and individual electrical contacts mounted to the interior of said housing for connecting said power supply via the electrical contacts to electrodes in said cassette that is inserted therein; and
   a touch screen display for independently monitoring and controlling an electrotransfer procedure in said cassette inserted in said housing.

2. The electrotransfer instrument of claim 1 wherein said housing comprises a front opening for sliding entry of said cassette.

3. The electrotransfer instrument of claim 1 wherein said housing comprises magnetic contacts to secure said cassette within said internal cavity.

4. The electrotransfer instrument of claim 1 further comprising an electrical relay that will engage said electrical contacts with said power source only when a cassette is inserted in said housing.

5. The electrotransfer instrument of claim 1 wherein said cassette further comprises a gel, a membrane, and buffer-wetted filter papers arranged in a stack.

6. The electrotransfer instrument of claim 5 wherein said cassette further comprises plate electrodes arranged in a stack, which are connected to said electrical contacts.

7. The electrotransfer instrument of claim 1 wherein said individual electrical contacts are spring-loaded electrical contacts.

8. The electrotransfer instrument of claim 1, further comprising grooves in the internal surfaces of the side walls of the cavity, wherein the grooves mate with ridges on the side of the cassette and align the cassette with the electrical contacts.

9. A method for transferring electrophoretically separated species from a slab gel to a sheet-form matrix, said method comprising:
   (a) placing said slab gel and a sheet-form matrix in an electroblotting cassette that comprises anode and cathode plates and external electrical contacts for each of said plates;
   (b) inserting said cassette in the electrotransfer instrument of claim 1 such that said external electrical contacts are in contact with said individual electrical contacts; and
   (c) imposing electrical charges on said electrodes to cause said species to migrate electrophoretically from said slab gel to said sheet-form matrix within said inserted cassette.

* * * * *